(12) United States Patent  (10) Patent No.: US 7,309,310 B2
Milbocker  (45) Date of Patent: *Dec. 18, 2007

(54) TREATMENT FOR GASTROESOPHAGEAL DISEASE

(75) Inventor: Michael T Milbocker, Holliston, MA (US)

(73) Assignee: Promethean Surgical Devices, Wrentham, MA (US)

( * ) Notice: Subject to any disclaimer, the term of this patent is extended or adjusted under 35 U.S.C. 154(b) by 237 days.

This patent is subject to a terminal disclaimer.

(21) Appl. No.: 11/086,620

(22) Filed: Mar. 22, 2005

(65) Prior Publication Data

US 2005/0247322 A1 Nov. 10, 2005

Related U.S. Application Data

(63) Continuation-in-part of application No. 10/118,785, filed on Apr. 9, 2002, now Pat. No. 7,047,980.

(51) Int. Cl.
*A61F 2/02* (2006.01)
*A61B 19/00* (2006.01)

(52) U.S. Cl. .................................. 600/30; 128/898
(58) Field of Classification Search ............... 128/898; 600/30; 604/508
See application file for complete search history.

(56) References Cited

U.S. PATENT DOCUMENTS

| | | | |
|---|---|---|---|
| 4,271,827 A | 6/1981 | Angelchik | |
| 5,088,979 A | 2/1992 | Filipi et al. | |
| 5,275,608 A | 1/1994 | Forman et al. | |
| 5,403,326 A | 4/1995 | Harrison et al. | |
| 5,448,990 A | 9/1995 | De Faria-Correa | |
| 5,571,116 A | 11/1996 | Bolanos et al. | |
| 5,709,854 A | 1/1998 | Griffith-Cima et al. | |
| 5,712,252 A | 1/1998 | Smith | |
| 5,763,399 A | 6/1998 | Lee | |
| 5,855,615 A | 1/1999 | Bley et al. | |
| 5,897,562 A | 4/1999 | Bolanos et al. | |
| 5,922,025 A | 7/1999 | Hubbard | |
| 5,976,526 A | 11/1999 | Atala | |
| 6,044,846 A | 4/2000 | Edwards | |
| 6,113,609 A | 9/2000 | Adams | |
| 6,238,335 B1 | 5/2001 | Silverman et al. | |
| 6,251,063 B1 * | 6/2001 | Silverman et al. | 600/29 |
| 6,251,064 B1 | 6/2001 | Silverman et al. | |
| 6,277,392 B1 | 8/2001 | Klein | |
| 6,296,607 B1 | 10/2001 | Milbocker | |
| 6,303,137 B1 | 10/2001 | Dittgen et al. | |
| 6,325,798 B1 | 12/2001 | Edwards et al. | |
| 6,524,327 B1 | 2/2003 | Spacek | |
| 6,595,909 B2 | 7/2003 | Silverman et al. | |
| 6,702,731 B2 | 3/2004 | Milbocker | |
| 2002/0049363 A1 | 4/2002 | Milbocker | |

(Continued)

*Primary Examiner*—Thomas J Sweet
(74) *Attorney, Agent, or Firm*—Francis H Kirkpatrick; Kirk Patent Consulting

(57) ABSTRACT

A system includes an implantable polymer for increasing the dimensions of layers of tissue. In one embodiment, the implantable polymer is delivered transorally using an endoscope and an injection needle. The system allows for visualization and injection of polymer into an esophageal sphincter. Methods of treating gastroesophageal reflux disease include insertion of the distal portion of the injection needle into the esophageal tissue and injection of a polymer liquid to enlarge tissue dimensions. The polymer can be injected at several sites to distribute localized pressures and attain better distribution of the tissue bulking effect.

18 Claims, 13 Drawing Sheets

U.S. PATENT DOCUMENTS

2002/0049503 A1 4/2002 Milbocker
2003/0135238 A1* 7/2003 Milbocker .................. 606/231
2003/0194505 A1 10/2003 Milbocker
2004/0068078 A1 4/2004 Milbocker

* cited by examiner

TREATMENT FOR GASTROESOPHAGEAL DISEASE

This application is a continuation-in-part of co-pending U.S. application Ser. No. 10/118,785, filed Apr. 9, 2002 now U.S. Pat. No. 7,047,980.

BACKGROUND OF THE INVENTION

Field of the Invention

This invention relates generally to a method to treat sphincters, and more particularly to a method to treat esophageal sphincters in mammalian patients as a remedy for gastroesophageal disease.

Gastroesophageal reflux disease (GERD) is a disorder of the lower esophageal sphincter which allows stomach contents to reverse flow into the distal portion of the esophagus during digestion. Complications associated with GERD include heartburn, pulmonary disorders, chest pain, esophageal ulcers, esophagitis, Barrett's esophagus, and esophageal carcinoma.

Treatments for GERD include prescribed acid blockers for limiting gastric production of acid and acid neutralizers. The relief is generally short-term, and the drugs alleviate symptoms of GERD without correcting the underlying dysfunction of the esophageal sphincter.

Various surgical procedures have been in use to correct GERD. In one surgical procedure, Nissen fundoplication, a portion of the gastric fundus is wrapped around the esophagus. The wrapped gastric fundus applies pressure to the esophagus to limit reverse flow of the stomach contents into the esophagus. All the surgical options require a large incision to expose the stomach and the lower esophagus. In laparoscopic procedures, a plurality of smaller incisions are formed in the abdominal wall to insert instruments into the body of the patient. Surgical procedures are expensive and can require significant amounts of recovery time.

Other surgical procedures, such as those disclosed in U.S. Pat. No. 5,403,326 and in U.S. Pat. No. 5,571,116, use surgical staples to secure the fundus of the stomach and the lower esophagus. Staples however, tend to concentrate stresses and could allow for tearing or necrosis of tissue. Movement of the stapled patient also contributes to staple damage. Such rigid instruments are inserted into the operative field with trocar type devices which make abdominal wall penetrations. The abdominal wall penetrations increase the risk of post-operative hernia, accidental organ perforation, or other drawbacks associated with surgical procedures.

U.S. Pat. No. 4,271,827 to Angelchik describes a sutureless procedure for treating GERD when the esophageal junction is positioned above the diaphragm. In this invention a C-shaped cushion prosthesis is disposed about the distal esophagus. The prosthesis prevents motion of the esophagus with respect to the diaphragm. It is not meant to aid the esophageal sphincter in its operation by decreasing the diameter of the esophageal sphincter. The inside diameter of the prosthesis corresponds to the normal outside diameter of the distal esophagus.

U.S. Pat. No. 6,044,846 to Edwards describes a method of treating a sphincter with a catheter that delivers energy to tissue. The energy delivery device has a tissue piercing distal end. Energy is delivered to the sphincter tissue to create necrosis in the sphincter to reduce sphincter relaxation. It does not direct bulk or thicken sphincter tissue.

U.S. Pat. No. 6,251,064 to Silverman et al. describes an implant for treatment of sphincters that involves formation of a solid in situ by precipitation. The implant does not contain functionality and cannot bond to tissue or form a solid implant through polymerization.

U.S. Pat. No. 6,277,392 to Klein describes a tissue augmentation implant for treatment of GERD. The implant is composed of particulate suspended in a liquid carrier. The implant differs from the present invention in that it does not form a solid in the body.

U.S. Pat. No. 6,303,137 to Dittgen et al describes an implant that forms a coagulant in situ due to its insolubility in water. The described precipitation reaction provides a solid implant, but differs from the present invention in that the functional end groups of the implant do not form bonds with the patient's tissue.

All of the above inventions differ from the present invention in that the present invention seeks to increase the functionality of the esophageal sphincter by bonding to and bulking the tissue of the lower esophageal sphincter. The tissue bulking increases the tension in the sphincter, creating increased resistance to reflux. The tissue bonding prevents erosion of the tissue around the implant and thus prevents loss of the implant.

It is thus an object of the present invention to provide a gastroesophageal treatment which overcomes the deficiencies of the prior art, and improving upon them to provide an improved method for treating a mammalian lower esophageal sphincter while reducing the frequency and quantity of reflux to which it is subject.

It is a further object of the present invention to provide a device and method to bulk sphincter tissue and to minimize injury to a mucosal layer of the sphincter.

It is yet another object of this invention to provide a method to controllably increase the bulk of a sphincter without creating a permanent impairment of the sphincter's ability to achieve a physiologically normal state of closure.

It is another object of this invention to provide a method to create a tightening of a sphincter without permanently damaging anatomical structures near the sphincter.

It is still yet another object of this invention to provide a method for controllably increasing the volume and geometry of a lower esophageal sphincter to reduce the frequency and quantity of stomach reflux.

It is yet a further object of this invention to provide an implant that forms a solid by self-polymerization within the patient's body, with no loss of water from the injectate of the present invention by precipitation or otherwise, to create an implant of known and constant and hence accurate volume, where the implant bonds to tissue at the implant site, and is resistant to absorption by the patient's body, and where the implant being the volume of the injectate.

BRIEF DESCRIPTION OF THE INVENTION

The present invention provides an improved method for treating a sphincter and for reducing the frequency and quantity of reflux by bulking the patient's sphincter tissue with an implant to also create a tightening of a sphincter without permanently damaging anatomical structures near the sphincter. The implant forms a solid by self-polymerization in the patient's body, bonds to esophageal tissue at the implant site, and is resistant to absorption by the patient's body.

The invention is provided in a method of treating a sphincter that provides a catheter means and an injection means coupled to the catheter means. The injection means includes a biocompatible implant to be delivered into the esophageal tissue. The injectable means has a tissue piercing distal end. The catheter means is introduced into an esophagus. A sphincter exterior surface is pierced with the injection means. The injection means is advanced a sufficient distance into an interior of the sphincter to a tissue site. Implantable polymer is controllably delivered to the interior of the tissue site. Controlled bulking is created in the sphincter to reduce sphincter dysfunction.

In one preferred embodiment of the present invention, a sphincter treatment apparatus delivers a polymer to a target tissue site to produce tissue-bulking in a mammalian sphincter, such as the lower esophageal sphincter (LES). In this embodiment, the sphincter treatment apparatus comprises a flexible elongate shaft delivered in a viewing endoscope also called catheter having a distal extremity known as an injection needle. The needle is coupled to a syringe containing the polymer implant to produce the tissue bulking. The injection means includes a tissue piercing distal end to deliver polymer to a portion of the sphincter. The sphincter treatment apparatus has an elongate shaft that connects by a standard luer connection to a syringe containing the polymer implant material. A pressure applied to syringe plunger injects polymer implant material into the lumen and the needle. The treatment apparatus is preferably guided by an endoscope having a steering and visualization means. The catheter end is configured to be positionable in a sphincter or adjacent anatomical structure, such as the cardia of the stomach. The catheter has sufficient length of about 40 to 240 cm. to position catheter end in the LES and/or stomach using a trans-oral approach. The catheter has at least one lumen for the delivery of the polymer injectate. It should be noted that catheters of the type described above are suitable for use in convention endoscopes with a viewing and steering means for achieving the methods set forth below.

The first several layers of sphincter consist of a mucosal layer, a submucosal layer and an underlying smooth muscle layer. The injection needle is preferably positioned to produce controlled tissue bulking in the smooth muscle layer underlying the mucosal and submucosal layers. More specifically, the needle is positioned to inject controlled amounts of polymer in the portion of smooth muscle tissue that lies approximately 1-4 mm from the surface of mucosal layer. The injection needle has an opening directed away from the mucosal layer. The opening of the needle extends into the sphincter wall and allows for delivery of the polymer to an optimal site within the smooth muscle layer.

In a further embodiment of the method for using sphincter treatment apparatus of the present invention, the sphincter treatment apparatus is first introduced into the esophagus under local anesthesia and positioned at target tissue site. The sphincter treatment apparatus may be introduced into the esophagus by itself or through a lumen in an endoscope (not shown), such as disclosed in U.S. Pat. Nos. 5,448,990 and 5,275,608, incorporated herein by reference, or a similar esophageal access device known to those skilled in the art. The diagnostic phase of the procedure may then begin and may be performed using a variety of diagnostic methods, including, but not limited to, the following: (i) visualization of the interior surface of the esophagus via an endoscope or other viewing apparatus inserted into the esophagus, (ii) visualization of the interior morphology of the esophageal wall using ultrasonography to establish a baseline for the tissue to be treated, or (iii) various manometry techniques, as are known in the art, for determining sphincteric integrity.

The treatment phase of the procedure begins after the diagnostic phase wherein the delivery of the polymer to target tissue site may be conducted under visual feedback control. A second diagnostic phase may be included after the treatment is completed, or after each injection of the polymer into the target site. This second diagnostic review provides an indication of LES tightening treatment success, and whether or not additional treatment is needed, and how the geometry of the implant locations is affecting LES function. It will be appreciated that the above procedure is applicable as further embodiments in whole or part to the treatment of other sphincters in the body.

The number and volume of injections in the LES or sphincter may vary. It is desirable to achieve tissue bulking in the range of 1-10 ml per site and produce implants at depths ranging from 1-4 mm from the interior surface of the LES or the sphincter wall. Since the implant is incompressible, the tension is translated to surrounding tissue. The result is tightening of the sphincter tissue. These changes are reflected in the transformed sphincter geometry.

It is desirable that these polymer implants are located predominantly in the smooth muscle layer of selected sphincter at depths ranging from 1-4 mm from the interior surface of the sphincter wall. Accordingly, the diameter of the polymer implants may vary between 1 to 10 mm. It is preferable that the polymer implants are less than 10 mm in diameter in order to reduce the risk of ischemic damage or pressure necrosis of the mucosal layer. In one preferred embodiment, a 2 mm diameter polymer implant is centered in the wall of the smooth muscle which provides a 2 mm buffer zone to prevent damage to the mucosa, submucosa and adventitia, while still allowing for blood flow. Also, those polymer implants may vary in both number and position within the esophagus or other sphincter.

It is desirable to implant a polymer that accentuates or augments the natural geometry of a sphincter. Such a polymer is preferably implanted in a particular locus of the LES defined by the natural undulated profile or inner fold of the sphincter. This approach results in maximal filling of the lumen of the LES with minimal polymer implant volume displaced away from the lumen. Injection into that particular locus serves to augment the natural protuberance of the sphincter tissue without relying primarily on an overall tightening of the sphincter. This results in improved sphincter function, especially with respect to a desirable sphincter opening.

Peristaltic motion in the esophagus is characterized by a locus of a contracted esophagus tissue that travels toward the stomach. It is preferred that the polymer implant have the same modulus as the surrounding body tissue. Then the force per unit area, or pressure, generated around the locus deforms both the tissue and the implant similarly. Therefore no net pressure discontinuity occurs across the tissue/implant interface that could cause tissue/implant decoupling and eventually implant erosion. However, under repeated net pressure action, an implant may decouple from the implant site and migrate through the tissue, usually toward the stomach. Furthermore, a ring geometry for the implant will increase erosion forces. A spherical implant may be compressed in one direction and may expand in two directions. A torus on the other hand can expand in only one direction, and is actually compressed in two directions. The compression of the torus is due to an overall contraction of the esophagus annulus and consequently the implant ring circumference.

The modulus of the present invention can be tailored to the modulus of the surrounding tissue by adjusting the amount of saline or other aqueous solution mixed with the polymer prior to implantation into the target site. For example, a ratio of 80:20 saline to polymer has been found to match sphincter tissue compliance. Such modulus matching is one way to reduce the likelihood of implant migration. Therefore modulus adjustability is a critical feature. Precipitation implants that form a solid upon contact with tissue or water have a set modulus, and that modulus is characteristic of the dissolved polymer in the implant. Varying the percentage of dissolved polymer will not change the final implant modulus, since the precipitated polymer and body fluid reach a characteristic equilibrium regardless of the initial implant polymer concentration.

A second cause of implant erosion is when the implant evokes an inflammatory reaction. Implants that are absorbed over time present a constantly changing surface to the body that evokes an infiltration of cells and a release of inflammatory compounds. The inflammation may also be caused by the hydrophobic nature of the implant. For example, PTFE, which is hydrophobic, generally provokes a marked inflammatory response even though it is chemically neutral.

The present invention creates a water interface at the tissue/implant interface. At water concentration greater than 10%, a hydrogel is formed that contains mobile water molecules that migrate to the implant surface preventing protein deposition and a hydrophilic layer.

A third cause of implant erosion is a lack of connectivity between the implant and surrounding tissue. Most tissue structures, even those formed in layers, are bound together so that perturbations of the tissue result in coupled motion between the layers of tissue. In general, uncoupled or relative motion between tissue parts results in inflammation. Usually the body counters this inflammation by forming an adhesion joining the rubbing tissue parts. There are a few notable exceptions such as the pericardium of the heart, which allows the heart to beat unhindered by attachment to surrounding tissue. This relative motion is however achieved by forming a liquid (noncellular) layer between the beating heart and the pericardium. When the pericardium is removed, it is common for adhesions to form between the heart and surrounding tissue. Furthermore, without the presence of a lubricant, relative motion between tissue structures naturally leads to wearing away of tissue and erosion.

Many of the features that make implants biocompatible, such as chemical inertness, also prevents adhesions from forming between the implant and the tissue. Thus relative motion is common. The present invention is an implant that not only forms a permanent solid known-volume implant within the body, but also forms a bond between the implant and surrounding tissue, which bond being comprised primarily of water.

Therefore, high water content, permanence of implant, modulus matching and tissue bonding are key features of the present invention that prevent implant erosion.

Tissue necrosis plays a role in implant erosion. From a purely mechanical point of view, introducing an incompressible volume into a confined space defined by incompressible tissue will result in high internal implant pressure. That pressure is simply the minimum force per unit area required to tear tissue to cause the space to enlarge. Since that pressure is always nonzero, the implant will always be implanted in a high pressure environment. This fact has two consequences. One, if the implant does not solidify quickly in the body much of the implant may be lost through the delivery hole. Two, if the implant does solidify quickly high internal pressure will persist resulting in clamping of local blood supply and pressure death of cells, both of which cause tissue to necrose around the implant. Under these conditions a chemically inert implant is treated by the body as a non-biocompatible foreign object, and the concomitant process to eliminate the implant ensues.

The present invention includes a delivery means that has features that are both unique and critical for acceptance of the implant by the body. The delivery device can take on a number of forms known in the art, and two examples are given here. The common feature of the examples is that the delivery device must however, provide a means for creating a pocket in the target tissue. This pocket may be formed before, during or after delivery of the implant solution so as to achieve optimal location, shape and reduction of implant pressure.

The simplest delivery means is a catheter tip which consists of a catheter preferably having a 7 Fr. outer dimension and a 4 Fr. inner dimension, with a 23-18 gauge needle tip extension. The tip of the needle will have a spade shape, the edges of which are sharp. Generally the width will be less than 2.3 mm (diameter of a 7 Fr. catheter), and more preferably 2.0 mm. The tip may be shielded while it is introduced into the endoscope to prevent damage to channel surfaces. The shield may be formed of a biocompatible wax that can pass safely through the digestive tract. The shield may be removed after introduction of the catheter into the endoscope or removed at the site of injection by actuating the endoscope in a manner which will cause the shield to pop off the needle tip.

Under visualization provided by the endoscope, the needle tip is directed to a site for injection and the tip introduced into the tissue a distance of 1-4 mm. One at the proper depth, a small amount of implant may be introduced into the body to confirm proper tip placement. Then by manipulating the endoscope, the needle can produce a cutting action that serves to form a pocket in the delivery site. Additional implant can be injected to give volume to the implant site and further direct cutting action of the needle tip. Once a desired profile is achieved the pocket can be filled to a desired volume. If the tissue appears to be under tension further enlargement of the pocket is possible. The result is a low tension implant.

The formation of pockets in tissue are common, and can be achieved in one embodiment by a needle delivery of a balloon. In this embodiment a double lumen catheter would be employed, one lumen of which is in fluid communication with the balloon and the other lumen connected to the exit port of the needle. Thus the balloon can be inflated independently of the delivery of implant. A pocket can thus be formed by introducing the needle/balloon combination to a tissue site, inflating the balloon to form a pocket, and then deflating the balloon and filling the pocket with the polymer implant.

Alternatively saline may be used to form the pocket without the use of a balloon, but in this approach the saline must be removed before the implant is introduced into the site. Due to the high affinity of the polymer of the present invention to the uptake of water, the removal of saline is not as critical as for other implant embodiments. For example, for a "precipitating" implant there is normally an excess of carrier fluid present in the implant volume which must be absorbed by the body. This plus any residual saline in the pocket contribute to shrinking of the effective volume of the prior art implant as the saline and the carrier are absorbed by the body.

The invention thus comprises a method of treating a mammalian sphincter in an esophagus of a patient with an injectable liquid polymer implant to reduce sphincter reflux, comprising: providing a catheter and an injector coupled to the catheter, the catheter having a tissue piercing needle distal end; introducing the catheter into the esophagus of the patient; piercing an exterior surface of the sphincter of the esophagus of the patient with the tissue piercing needle distal end on the catheter; advancing the tissue piercing needle distal end a distance in an interior of the sphincter to a tissue site; and controllably delivering the injectable polymer into the tissue site and create a controlled, volume-constant implant in the sphincter to reduce the frequency and quantity of sphincter reflux. The sphincter may be a lower esophageal sphincter. The sphincter may be an upper esophageal sphincter. The volume of implant may comprise a bolus of a diameter of about 1-10 mm injected to the lower esophageal sphincter to reduce lower esophageal motion. The volume of implant may comprise a bolus of a diameter of about 1-10 mm injected into the lower esophageal sphincter to reduce the frequency of reflux of stomach contents into an esophagus. The volume of implant may comprise a bolus of a diameter of about 1-10 mm and is implanted in the lower esophageal sphincter to reduce a frequency of a symptom of reflux of stomach contents into an esophagus. The volume of implant may comprise a bolus of a diameter of about 1-10 mm injected into the lower esophageal sphincter to reduce an incidence of a sequela of reflux of stomach contents into an esophagus. The polymer delivery device may deliver the volume of polymer to a submucosa of the sphincter. The polymer implant may comprise a biocompatible polymer which polymerizes in situ. The polymer implant may comprise a biocompatible polymer, which initiates a fibrotic response. The polymer implant may comprise a compound of polyisocyanate capped polyol and free polyisocyanate. The polymer implant may comprise a compound of isophorone diisocyanate capped copolymer of polypropylene and polyethylene oxide and free isophorone diisocyanate. The polymer implant may comprise a compound of toluene diisocyanate capped copolymer of polypropylene and polyethylene oxide and free toluene diisocyanate. The catheter may be directed to the sphincter transorally. The catheter may be directed to the sphincter transorally through an endoscope.

The invention may also comprise a method of treating a mammalian sphincter in the esophagus of a patient by implantation of a bolus of a polymer therein, the method comprising: coupling a catheter and a polymer needle delivery device together, the polymer delivery device including a tissue injection needle sized to be positioned within the tissue of the sphincter; introducing the catheter into an esophagus of the patient; positioning the polymer delivery needle device in a tissue target site of the sphincter; and controllably delivering the polymer volume and mix to the sphincter wherein the polymer bonds to the tissue and to create a controlled tissue bulking of the sphincter to reduce the frequency of sphincter relaxation. The sphincter may comprise a lower esophageal sphincter. The sphincter may comprise an upper esophageal sphincter. The bolus of polymer may have a diameter of 1 to 10 mm and may be injected into the lower esophageal sphincter to reduce the duration of lower esophageal sphincter relaxation. The bolus of polymer may be injected into the lower esophageal sphincter to reduce a frequency of reflux of stomach contents into an esophagus. The bolus of polymer may be injected into the lower esophageal sphincter to reduce a frequency of a symptom of reflux of stomach contents into an esophagus. The bolus of polymer may be injected into the lower esophageal sphincter to reduce an incidence of a sequela of reflux of stomach contents into an esophagus. The bolus of polymer may be delivered to the sphincter to cause a reduction in the opening of the sphincter. The bolus of polymer may be delivered to the sphincter to cause a tissue contraction around the implant. The polymer delivery device may deliver the polymer to create a tightening of the sphincter without permanently damaging anatomical structures near the sphincter. The polymer delivery device may deliver the polymer to a lower esophageal sphincter without permanently disrupting an aorta positioned near the lower esophageal sphincter. The polymer delivery device may deliver the polymer to a lower esophageal sphincter without permanently damaging a vagus nerve positioned near the lower esophageal sphincter. The polymer delivery device may deliver the polymer to a lower esophageal sphincter without permanently damaging an esophageal plexus of nerves and veins positioned near the lower esophageal sphincter. The polymer delivery device may deliver the polymer to a lower esophageal sphincter while preserving a blood supply to the lower esophageal sphincter. The polymer delivery device may deliver the polymer to the sphincter to create a tissue bulking volume in a submucosa of the sphincter. The polymer delivery device may include a biocompatible polymer which polymerizes in situ. The polymer delivery device may include a biocompatible polymer which initiates a fibrotic response. The polymer delivery device may include a polymer which is comprised of polyisocyanate capped polyol and free polyisocyanate. The polymer delivery device may include a polymer which is comprised of isophorone diisocyanate capped copolymer of polypropylene and polyethylene oxide and free isophorone diisocyanate. The polymer delivery device may include a polymer which is comprised of toluene diisocyanate capped copolymer of polypropylene and polyethylene oxide and free toluene diisocyanate. The polymer delivery device may be delivered to the sphincter transorally without an endoscope means. The polymer delivery device may be delivered to the sphincter transorally with an endoscope means.

BRIEF DESCRIPTION OF THE DRAWINGS

The objects and advantages of the present invention will become more apparent when viewed in conjunction with the following drawings in which.

DETAILED DESCRIPTION OF THE PREFERRED EMBODIMENTS

Figure 1:
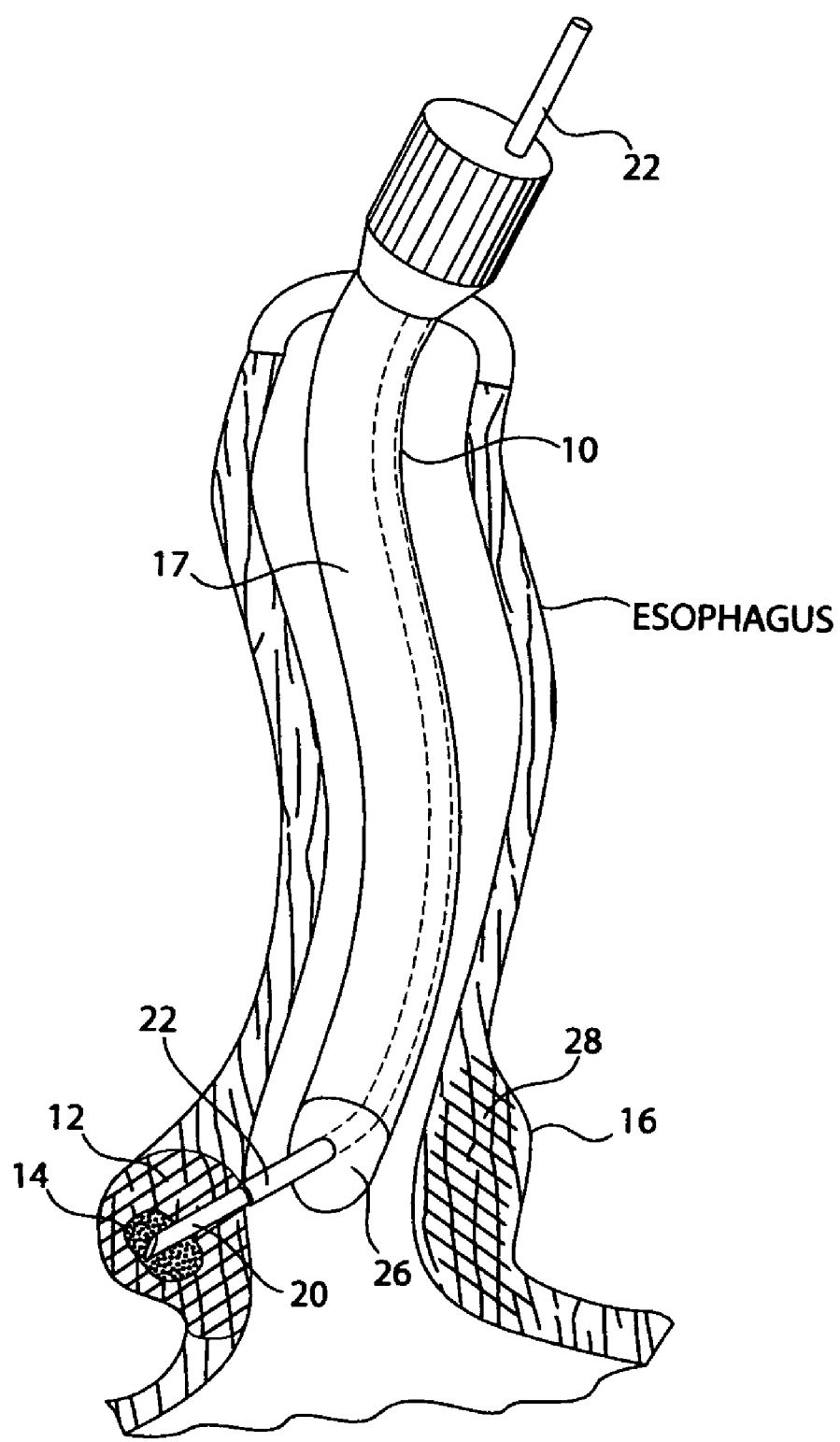
FIG. 1 is an illustrated lateral view of the upper GI tract illustrating the positioning of the sphincter treatment apparatus of the prior art (U.S. Pat. No. 6,040,846) in the lower esophageal sphincter.
Figure 2:
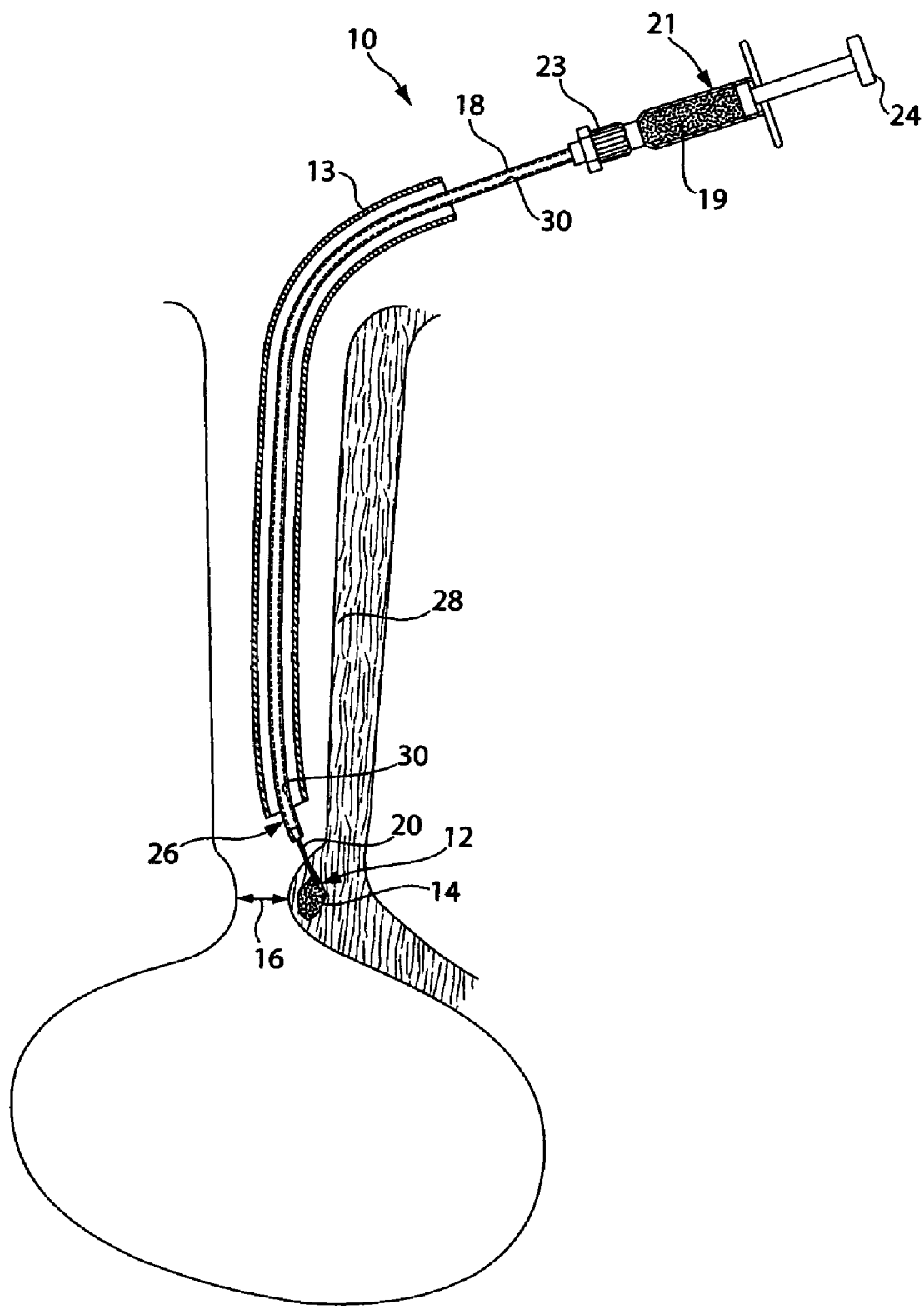
FIG. 2 is a lateral view of the present invention positioned in the upper GI tract illustrating the catheter lumen, catheter end polymer injectable delivery device, syringe and injectate.

Referring now to the drawings in detail, and particularly to FIGS. 1 and 2, in FIG. 1 a prior art embodiment of a sphincter treatment apparatus 10 is shown which delivers polymer to a target tissue site 12 in esophagus 28 to produce tissue-bulking implant 14 in a sphincter 16, such as the lower esophageal sphincter (LES). In this embodiment, sphincter treatment apparatus 10 comprises a flexible elongate shaft comprising a viewing endoscope 17, also called a catheter, with a distal extremity 26 carrying injection needle 20, which is in fluid communication with a syringe 21, not shown in FIG. 1. The injection means includes the tissue piercing distal end needle 20, which is configured to penetrate a fixed depth into a sphincter wall 28 and deliver polymer to a portion thereof.

FIG. 2 shows generally an apparatus 10 of the invention. As shown in FIG. 2, the flexible elongate shaft 18 of the sphincter treatment apparatus 10 connects to the syringe 21 containing polymer implant 19. The connection is made by a standard luer type connection 23. The Luer connection 23 allows fluid communication between the syringe 21 and a catheter lumen 30, and the needle 20. Pressure applied to the syringe plunger 24 injects the polymer implant 19 into the lumen 30 and then later into the needle 20. The distal end of the catheter 26 is configured to be positionable in a sphincter 16 such as the LES or adjacent anatomical structure, such as the cardia of the stomach. The catheter 18 has sufficient length to position the needle end 20 in the LES and/or stomach using a trans-oral approach. Typical lengths for the catheter 18 include, but are not limited to, a range of 40-240 cm. The catheter 18 must have at least one lumen 30 for the delivery of the injectable polymer implant 19, which lumen 30 extends the full length of catheter 18. The injection needle 20 should include a pointed, beveled tip capable of delivering the injectable polymer 19. The opening may be of the type used in endoscopic injection systems. It should be noted that catheters of the type described above are suitable for use in conventional endoscopes with a viewing and steering means for achieving the methods set forth below.

Figure 3:
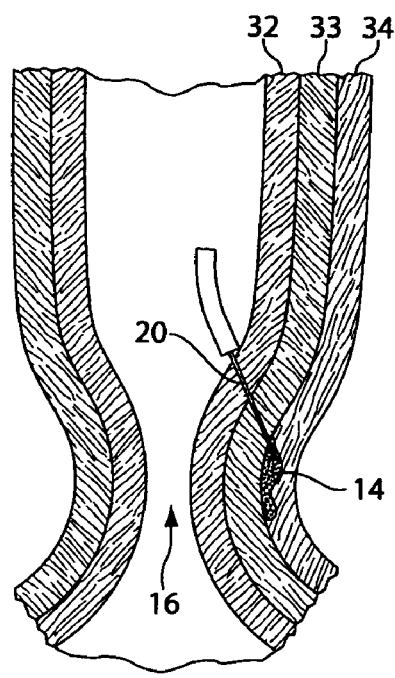
FIG. 3 is a lateral view of the injection needle and sphincter wall, illustrating the creation of a bulked tissue site.

The first several layers of a mammalian sphincter 16 is shown in FIG. 3, and consists of a mucosal layer 32, a submucosal layer 33 and an underlying smooth muscle layer 34. The injection needle 20 is positioned to produce controlled tissue bulking 14 preferably in the smooth muscle layer 34 underlying the mucosal and submucosal layers 32 and 33. More specifically, the needle 20 is positioned to inject controlled amounts of the polymer in the portion of the smooth muscle tissue 34 that lies approximately 1-4 mm from the surface of the mucosal layer 32.

Figure 4:
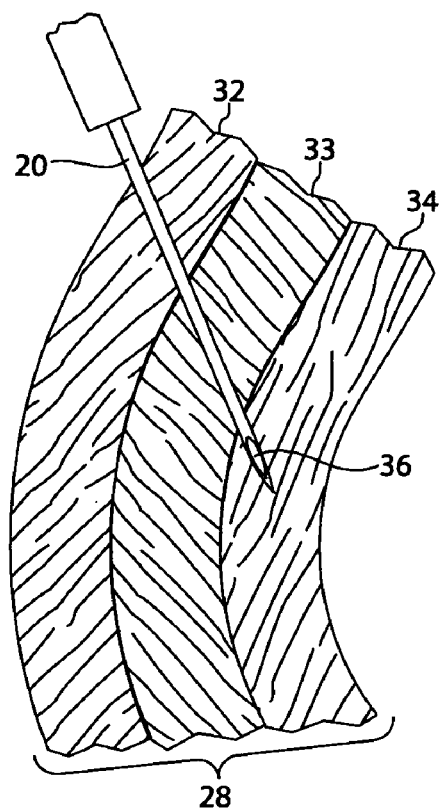
FIG. 4 depicts a cross sectional view of sphincter anatomy illustrating the layers of the sphincter wall.
Figure 5:
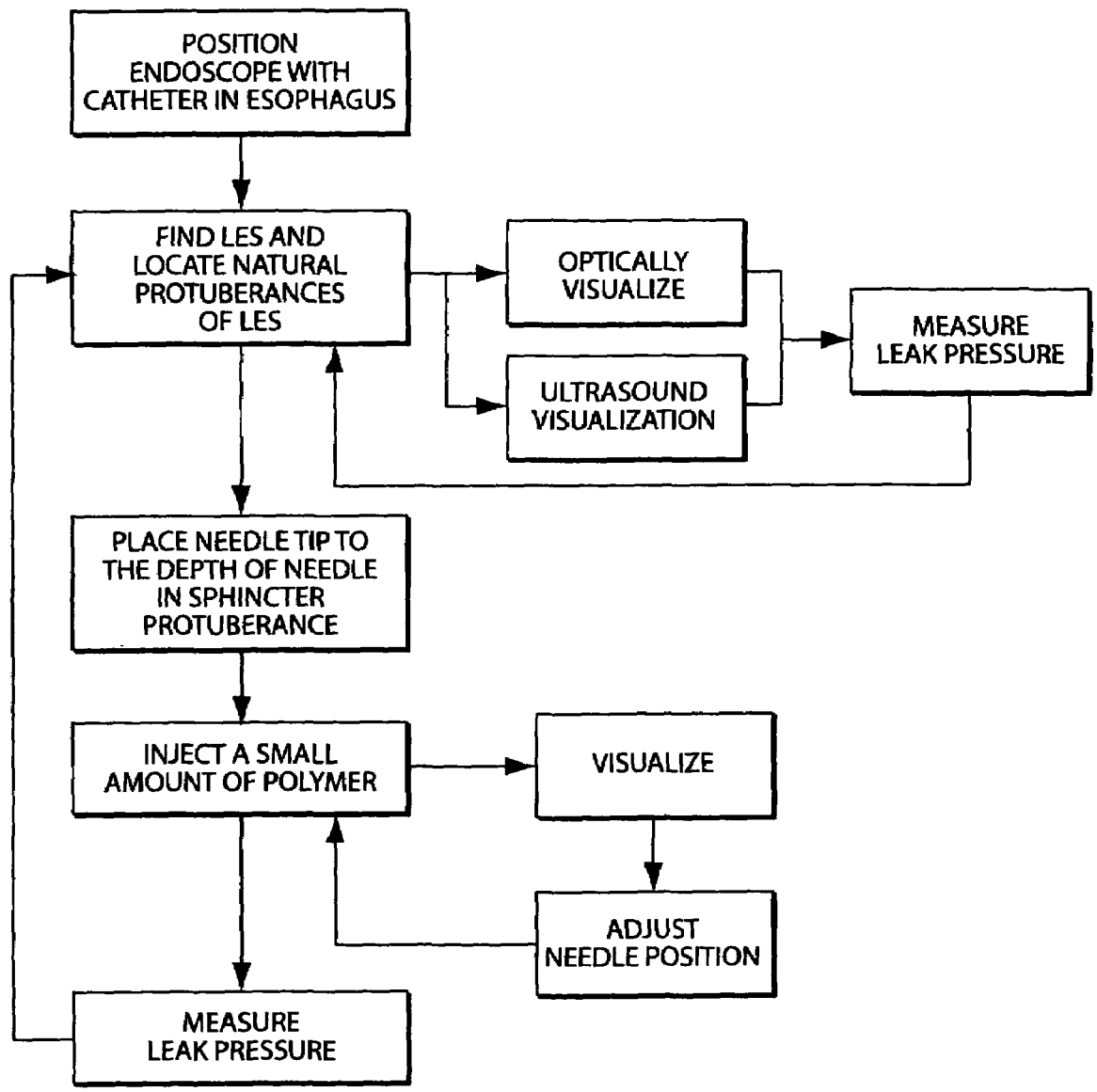
FIG. 5 is a flow chart illustrating a sphincter treatment method.

The injection needle 20 shown in FIG. 4 has an opening 36, directed away from the mucosal layer 32. The opening 36 of the needle 20 extends into the sphincter wall 28 and allows for delivery of the polymer to an optimal site preferably within the smooth muscle layer 34. FIG. 5 displays a flow chart illustrating a preferred embodiment of the method for using the sphincter treatment apparatus 10 of the present invention. In this embodiment, the sphincter treatment apparatus 10 is first introduced into the patient's esophagus under local anesthesia and positioned at the target tissue site 12. The sphincter treatment apparatus 10 can be introduced into the esophagus by itself or through a lumen in an endoscope (not shown), such as disclosed in U.S. Pat. Nos. 5,448,990 and 5,275,608, incorporated herein by reference, or a similar esophageal access device known to those skilled in the art.

The diagnostic phase of the procedure may be performed using a variety of diagnostic methods, including, but not limited to, the following: (i) visualization of the interior surface of the esophagus via an endoscope or other viewing apparatus inserted into the esophagus, (ii) visualization of the interior morphology of the esophageal wall using ultrasonography to establish a baseline for the tissue to be treated, and (iii) various manometry techniques, as are known in the art, for determining sphincteric integrity. After the diagnosis, the treatment phase of the procedure may begin by the delivery of a polymer to the target tissue site 12, and such delivery of polymer can be conducted under visual feedback control. A second diagnostic phase may be included after the treatment is completed, or after each injection. This provides an indication of LES tightening treatment success, whether or not additional treatment is needed, and how the geometry of the implant locations is affecting LES function. It will be appreciated that the above procedure is applicable in whole or part to the treatment of other sphincters in the body.

Figure 6:
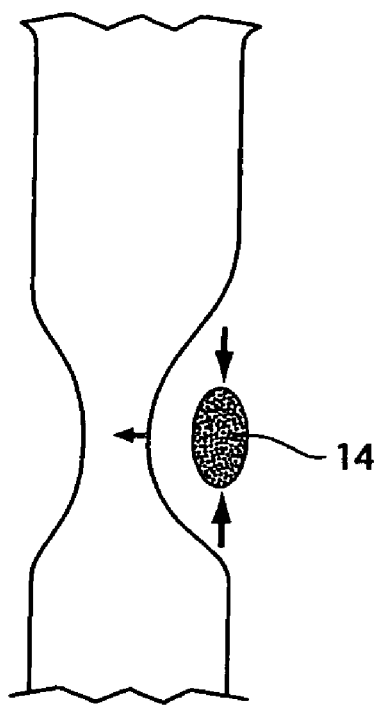
FIG. 6 shows forces created by implant 14 in the vessel wall.
Figure 7:
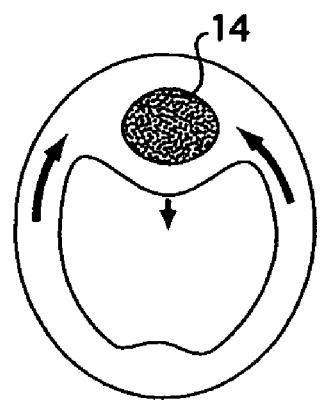
FIG. 7 illustrates tension in the sphincter tissue due to tissue bulking and tissue shrinkage caused by cell infiltration.

The number and volume of injections in the LES or sphincter 16 can vary. In a preferred embodiment, the polymer bulking material is utilized in the range of 1-10 ml per site and produces implants at depths ranging from 1-4 mm from the interior surface of the LES or sphincter wall 28. Since the implant is incompressible, the tension is translated to the surrounding tissue. The result is tightening of the sphincter tissue as depicted in FIG. 6. These changes are reflected in transformed sphincter geometry shown in FIG. 7. It is desirable that these implants 14 are predominately located in the smooth muscle layer of the sphincter 16 at depths ranging from 1-4 mm from the interior surface of the sphincter wall 28. Accordingly, the diameter of the implants 14 can vary between 1 to 10 mm. It is preferable that the implants 14 are less than 10 mm in diameter in order to reduce the risk of ischemic damage or pressure necrosis of the mucosal layer. In one preferred embodiment, a 2 mm diameter implant centered in the wall of the smooth muscle provides a 2 mm buffer zone to prevent damage to the mucosa, submucosa and adventitia, while still allowing for blood flow. Also, the implants 14 can vary in both number and position within the esophagus or the sphincter 16.

Figure 8:
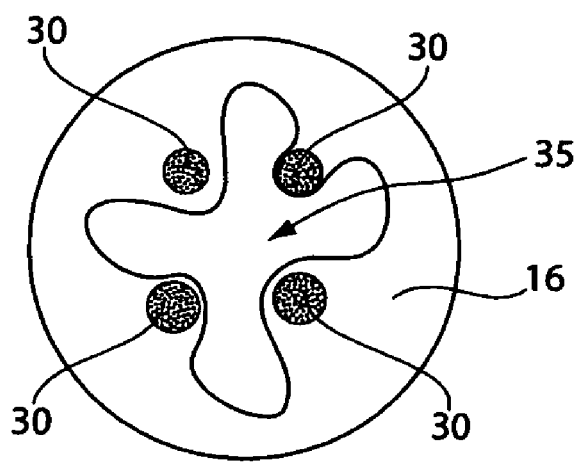
FIG. 8 is a lateral view of sphincter smooth muscle tissue illustrating multiple implanted volume configurations.
Figure 9:
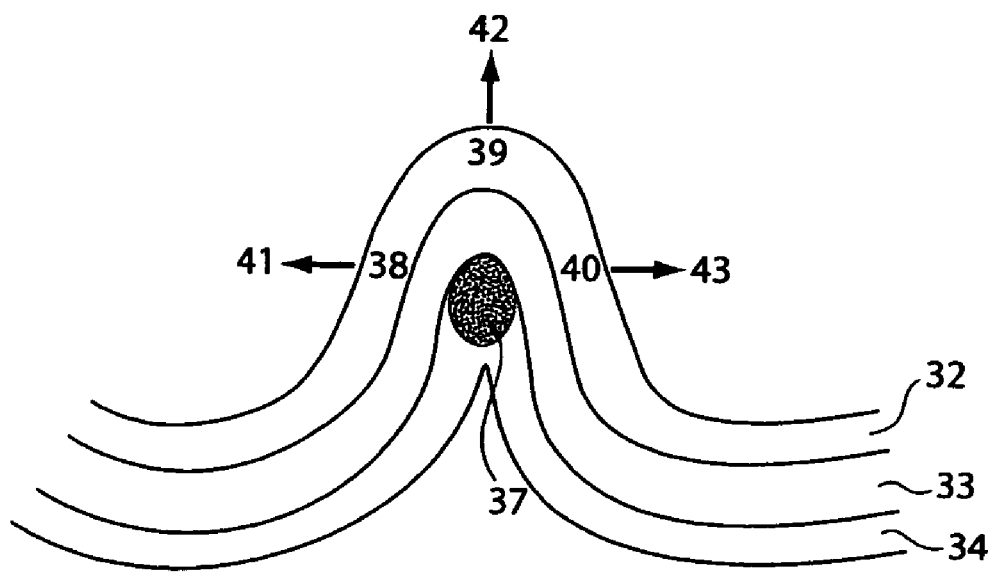
FIG. 9 shows a cross-sectional representation depicting forces on tissue by an implant.
Figure 10:
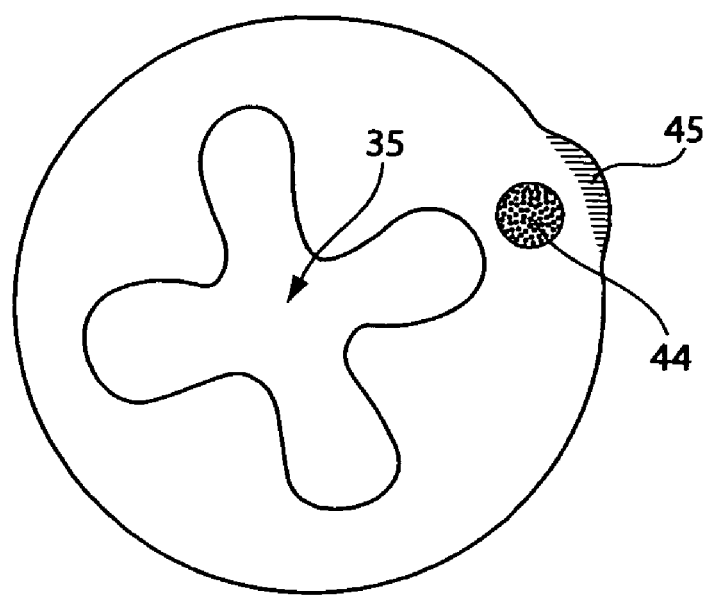
FIG. 10 represents a cross-sectional view of an esophagus with an off side implant.

It is desirable to implant the polymer so that it accentuates or augments the natural geometry of a sphincter. In FIG. 8, the polymer is depicted preferably implanted in a locus 30 of the LES defined by the natural undulated profile of the sphincter 16. This method of the invention has several advantages. The implant introduced at the site 37 depicted in FIG. 9 creates internal forces that displace adjacent tissue surfaces 38, 39, 40 in the direction indicated by arrows 41, 42, 43, respectively. The procedure in this embodiment results in maximal filling of the lumen 40 of the LES with minimal implant volume displaced away from the lumen. For example, the site shown in FIG. 10 illustrates an implant site 44 that produces displacement of implant outside 45 the lumen 40 of the LES. Injection into the locus 30 serves to augment the natural protuberance "P" of the sphincter tissue without relying primarily on an overall tightening of the sphincter. This results in improved sphincter function, especially with respect to desirable sphincter opening.

Figure 11A:
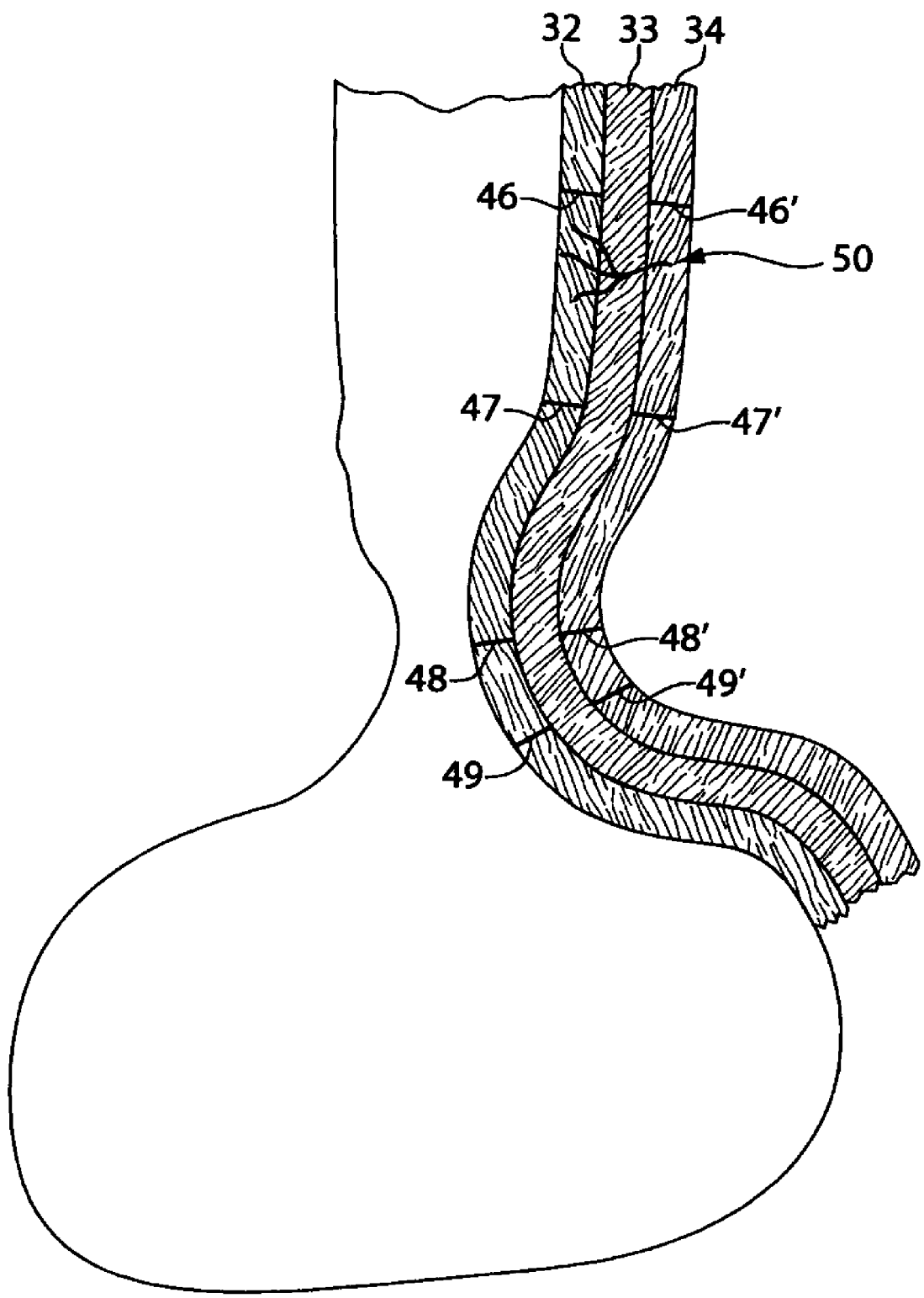
FIGS. 11a and 11b represent an undesired tissue augmentation display.
Figure 11B:
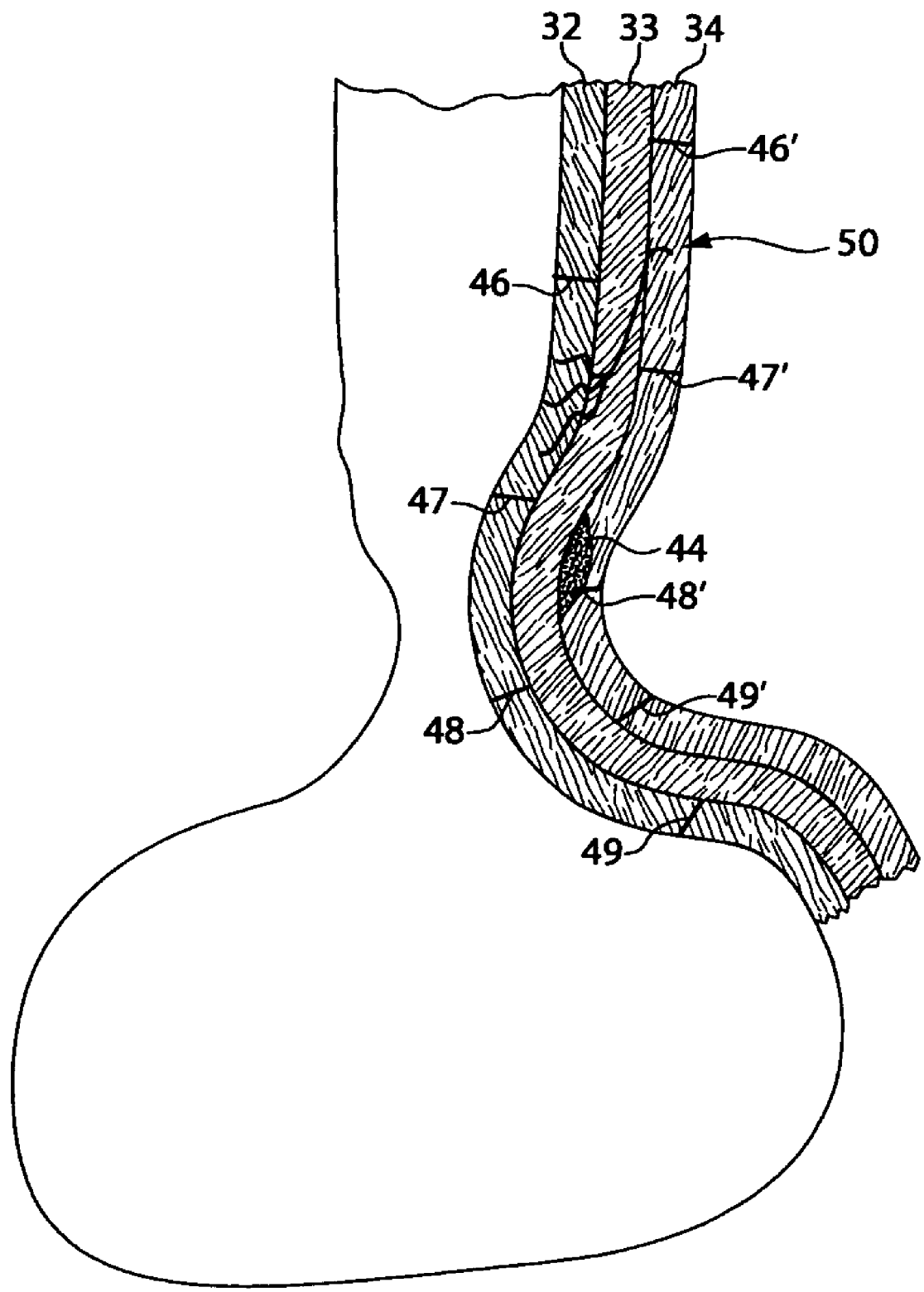
Figure 12:
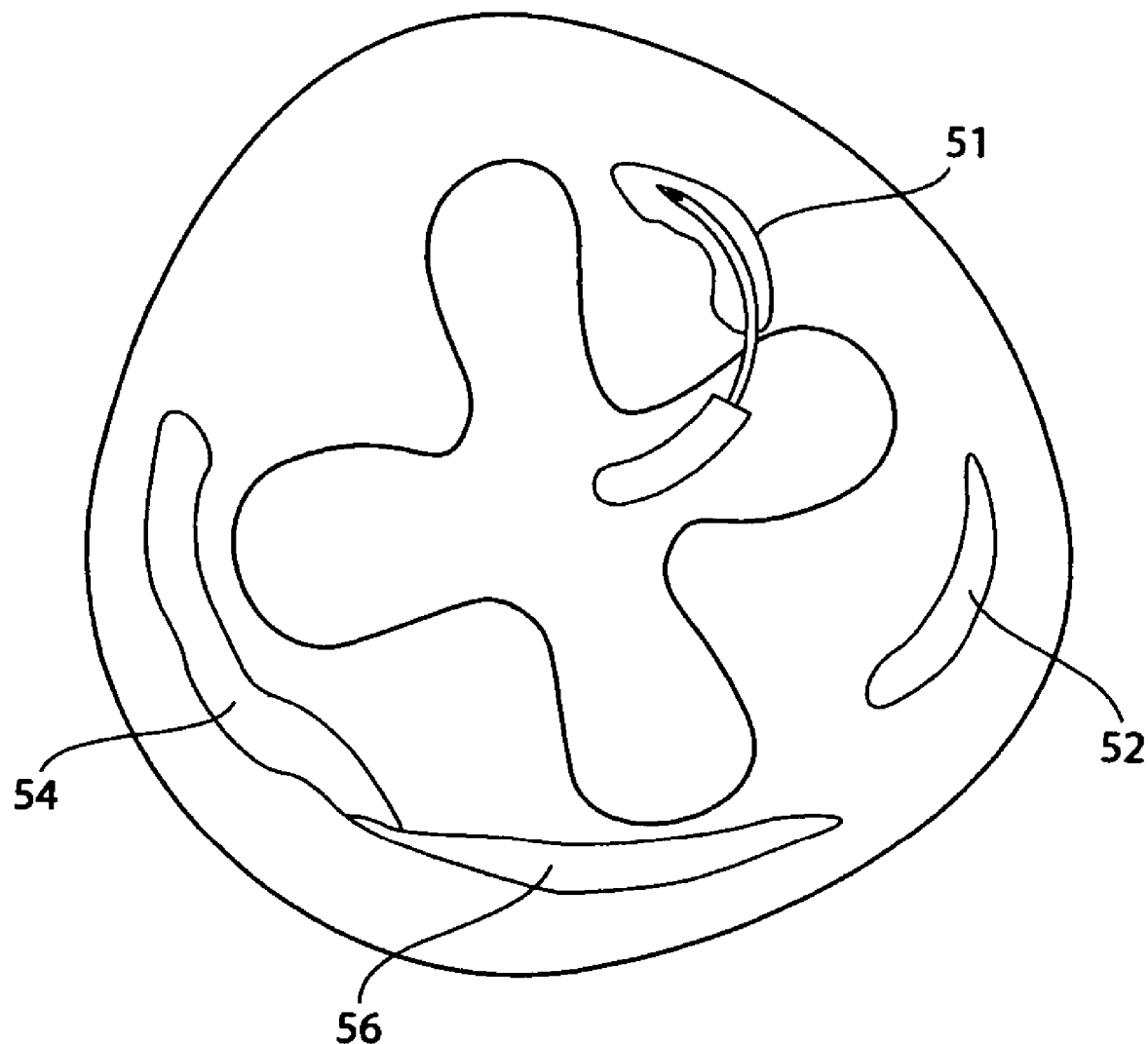
FIG. 12 shows a cross-sectional view of an esophagus with curved implants as an undesired tissue augmentation.

The representation shown in FIGS. 11*a* and *b* illustrate an undesirable method of sphincter augmentation. FIG. 11*a* shows the natural alignment of reference points on the mucosal layer 46, 47, 48, 49 and smooth muscle layer 46', 47', 48', 49'. When the implant is placed outside the preferred locus 30, the mucosal layer of the esophagus 32 is displaced as a whole toward the stomach as depicted in FIG. 11*b* by the misalignment of the aforementioned reference points. Since the blood vessels 49 travel through the smooth muscle layer to nourish the mucosal layer, displacement of the mucosal layer relative to the smooth muscle layer stretches the "blood" vessels 50. The vessels 50 can become occluded or rupture, thus resulting in ischemia of the mucosal layer. This may result in a worsening of the GERD symptoms, even if sphincter function is improved. FIG. 12 illustrates yet another undesirable method of sphincter augmentation. It is possible to use a curved needle or like instrument to form a channel of curvature 51 in the smooth muscle tissue of the LES. An implant may be injected during or after the formation of the curved channel 51 resulting in the implant conforming to this geometry and forming a curved implant 52. These implants may be joined as illustrated with 54 and 56. A single joined implant may be formed by injecting sufficient material that 51, 52, 54, 56 join circumferentially forming an encircling ring. The resulting encircling implant prevents the annulus formed by the LES to change. And while sufficient implant may be delivered to decrease the annulus diameter and thus reduce gastric reflux, it also compromises the annulus opening making it difficult to swallow. Additionally, the natural peristaltic motion of the esophagus is known to cause ring implants to erode into the stomach.

The primary cause of the implant erosion is believed to be due to a combination of factors, among them modulus differences between the implant and the surrounding tissue and the propensity of the implant to decouple or pull away from surrounding tissue. The latter may be exacerbated by inflammation, pressure necrosis and various chemical compounds excreted by infiltrating cells.

Figure 13A:
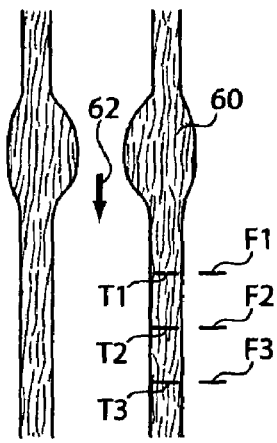
FIGS. 13a-13c depict peristaltic motion against a set of fixed references.
Figure 13B:
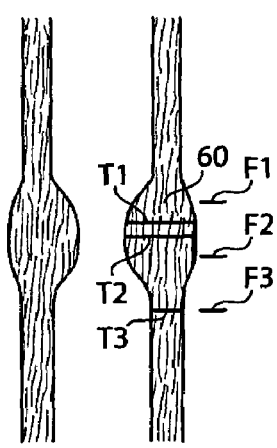
Figure 13C:
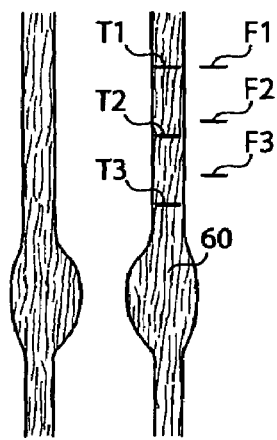

The series of drawings of FIGS. 13*a*, *b* and *c* represent the peristaltic motion referenced against a set of fixed coordinated F1, F2, F3. The peristaltic motion is characterized by a locus of a contracted esophagus that travels toward the stomach (not shown). In FIG. 13*a* the contraction locus 60 of the esophagus travels toward the stomach indicated by arrow 62. Note the alignment of fixed reference points F1-F3 and tissue reference points T1-T3. As the locus 60 travels through the reference points T1-T3 as shown in FIG. 13*b*, note that points T1-T3 contract together relative to coordinates F1-F3. And as shown in FIG. 13*c*, reference points T2 and T3 are stretched apart relative to coordinates F2-F3 as the locus 60 travels beyond the referenced tissue location.

Figure 14A:
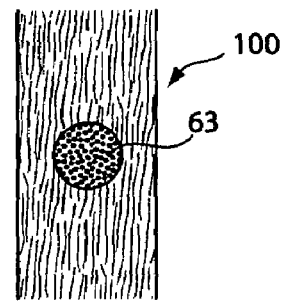
FIGS. 14a-14d represents a locus traveling an esophagus.
Figure 14B:
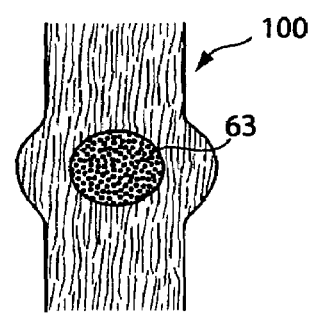
Figure 14C:
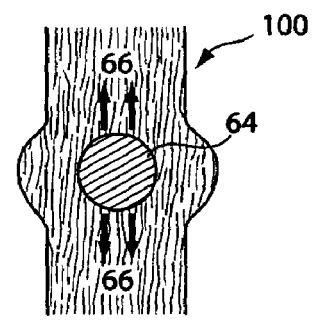
Figure 14D:
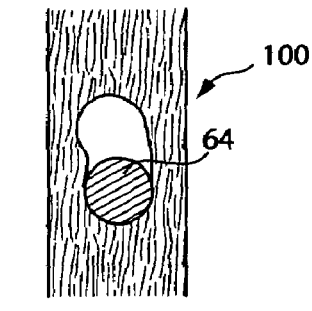

It is preferred that the implant of the present invention have the same modulus as the surrounding tissue. Then the force per unit area, or pressure, generated around the locus 60 deforms the tissue and the implant similarly. Therefore there is no net pressure discontinuity that occurs across the tissue/implant interface that could cause tissue/implant decoupling and eventually erosion in the present invention. FIG. 14*a* illustrates a cross section of the esophagus 100 in the relaxed states with a reference circle 63 fixed to the tissue. When the locus 60 travels through the circle it deforms the circle into an ellipse as depicted in FIG. 14*b*. However, as shown in FIG. 14*c*, a high modulus implant 64 implanted in the tissue will not deform in this way producing forces depicted by arrows 66 that tend to cause the implant to cut through the tissue. Under repeated action, the implant decouples from the implant site and migrates through the tissue, usually toward the stomach, as depicted in FIG. 14*d*. Furthermore, a ring geometry for the implant will increase erosion forces.

Figure 15A:
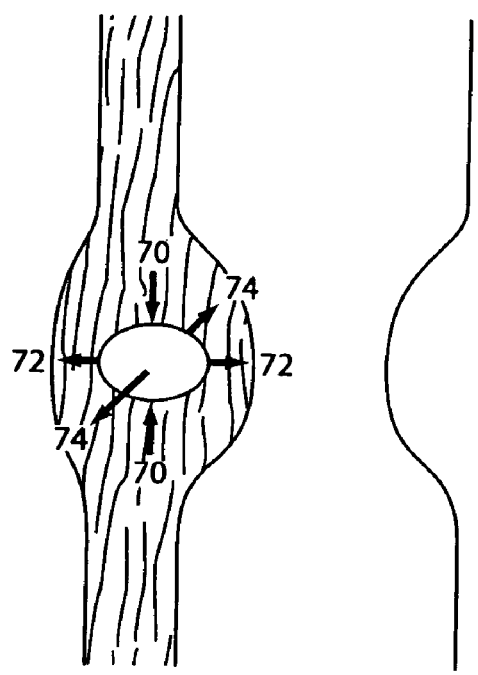
FIGS. 15a-15b represents forces generated on implants.
Figure 15B:
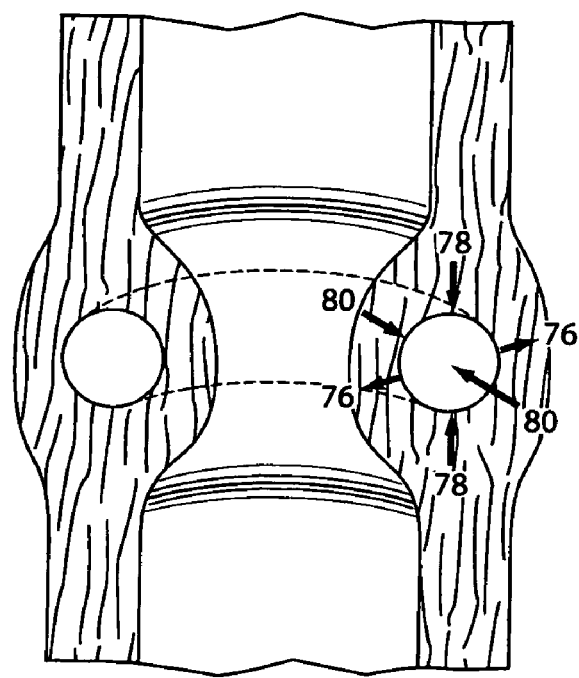

As shown in FIG. 15*a*, a spherical implant 69 will be compressed in one direction 70 and expand in two directions 72 and 74. A torus on the other hand can expand in only one direction 76, and is actually compressed in two directions, 78 and 80 as depicted in FIG. 15*b*. The compression is depicted along direction 80 due to an overall contraction of the esophagus annulus and consequently the implant ring circumference.

The modulus of the present invention can however be tailored to the modulus of the surrounding tissue by adjusting the amount of saline or other aqueous solution mixed with the polymer implant prior to implantation of the polymer. A preferred embodiment for such polymer solution is for example, a ratio of 80:20 saline to polymer, which ratio was found to match sphincter tissue compliance. Modulus matching is therefore one preferred way in the present invention to reduce the likelihood of implant migration. Therefore "modulus adjustability" is a critical feature. Precipitation implants that form a solid upon contact with tissue or water have a set modulus, and that modulus is characteristic of the formerly dissolved polymer in the implant. Varying the percentage of dissolved polymer will not change the final implant modulus, since the precipitated polymer and body fluid reach a characteristic equilibrium regardless of the initial implant polymer concentration.

A second cause of implant erosion is whether the polymer implant evokes an inflammatory reaction. Implants that are absorbed over time present a constantly changing surface to the body that evoke infiltration of cells and release of inflammatory compounds. Inflammation can also be caused by the hydrophilic nature of the implant. For example, PTFE, which is hydrophobic, generally provokes a marked inflammatory response even though it is chemically neutral. The present invention creates a water interface at the tissue/implant interface. At water concentration greater than 10%, a hydrogel is formed that contains mobile water molecules that migrate to the implant surface preventing protein deposition and a hydrophilic layer.

A third cause of implant erosion is a lack of connectivity between the implant and surrounding tissue. Most tissue structures, even those formed in layers, are bound together so that perturbations of the tissue result in coupled motion between the layers of tissue. In general, uncoupled or relative motion between tissue parts results in inflammation. Usually the body counters by forming an adhesion joining the parts. There are a few notable exceptions such as the pericardium of the heart, which allows the heart to beat unhindered by attachment to surrounding tissue. But this relative motion is achieved by forming a liquid (noncellular) layer between the beating heart and the pericardium. When the pericardium is removed, it is common for adhesions to form between the heart and surrounding tissue. Furthermore, without the presence of a lubricant, relative motion between tissue structures naturally leads to wearing away of tissue and thus effecting erosion.

Many of the features that make implants biocompatible, such as chemical inertness, also prevents adhesions to form between the implant and the tissue. Thus relative motion, because of no adhesion between adjacent tissue structures, is common. The present invention is an implant that not only forms a permanent solid implant within the body, but also forms a bond between the implant and surrounding tissue, that bond mostly composed of water.

Therefore, high water content, permanence of implant, modulus matching and tissue bonding are key features of the present invention that prevent implant erosion. However, tissue necrosis plays a role in implant erosion. Introducing an incompressible volume into a confined space defined by incompressible tissue will result in a high internal implant pressure. That pressure is simply the minimum force per unit area required to tear tissue to cause the space to enlarge. Since that pressure is always non-zero, the implant will always be implanted in a high pressure environment. This fact has two consequences. One, if the implant does not solidify quickly in the body much of the implant may be lost through the delivery hole. Two, if the implant does solidify quickly, high internal pressure will persist resulting in clamping of local blood supply and pressure death of cells, both of which cause tissue to necrose around the implant. Under these conditions a chemically inert implant is treated by the body as a non-biocompatible foreign object, and the concomitant process to eliminate the implant ensue.

Therefore, a preferred embodiment of the present invention includes a delivery means that has features that are both unique and critical for acceptance of the implant by the body. The delivery device may include several preferred embodiments. The common feature of these devices is that the delivery device must provide a means for creating a pocket in the target tissue. This pocket may be formed before, during or after delivery of the implant polymer solution so as to achieve optimal location, shape and reduction of implant pressure.

Figure 16:
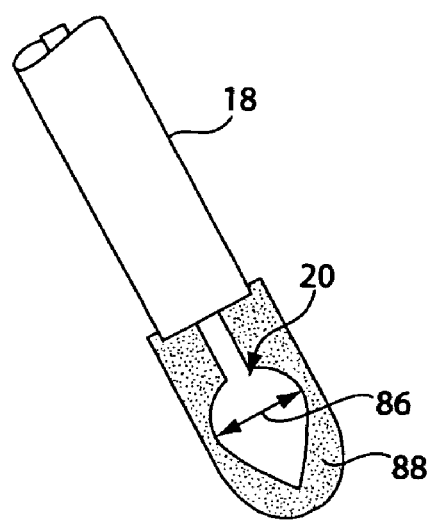
FIG. 16 shows an implant delivery arrangement.

The simplest delivery means is shown in FIG. 16, having a catheter tip 18, generally having a 7 Fr. outer dimension and a 4 Fr. inner dimension, with a 23-18 gauge needle tip extension 20. The tip of the needle 20 will have a spade shape, as shown in FIG. 16, the edges of which are sharp. Generally the width 86 of the needle tip 20 will be less than 2.3 mm (diameter of a 7 Fr. catheter), and more preferably 2.0 mm. The tip 86 may be shielded by a covering 88 of a biocompatible wax that can pass safely through the digestive tract while the tip is introduced into the endoscope to prevent damage to channel surfaces of that endoscope. The shield 88 may be removed after introduction of the catheter into the endoscope or removed at the site of injection by manipulably actuating the endoscope in a manner which will cause the shield 88 to pop off the needle tip 20.

Figure 17:
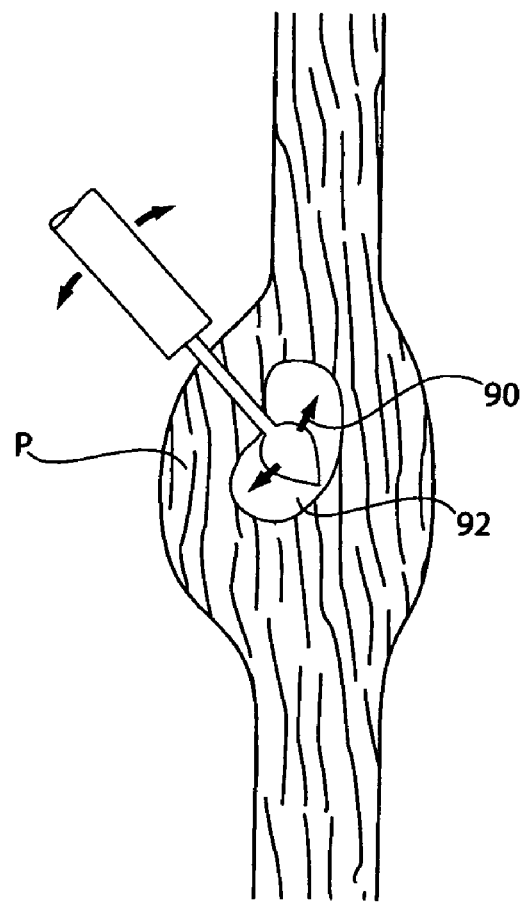
FIG. 17 shows an arrangement for cutting a pocket at a target site in an esophagus.

Under visualization provided by the components of the endoscope, not shown here for clarity, the needle tip 20 is directed to a site for injection and the tip introduced into the tissue a distance of 1-4 mm. Once at the proper depth of tissue, a small amount of polymer implant may be introduced into the body to confirm proper tip placement. Then by manipulating the endoscope supporting the needle 20, the needle 20 may produce a cutting action 90 as represented in FIG. 17, that action serving to form a pocket 92 in the delivery site 92. Additional implant can be injected to give volume to the implant site (preferably in a protuberance "P") and further direct cutting action of the needle tip. Once a desired profile is achieved the pocket can be filled to a desired volume. If the tissue appears to be under tension, further enlargement of the pocket is possible. The result is a low tension implant.

Figure 18:
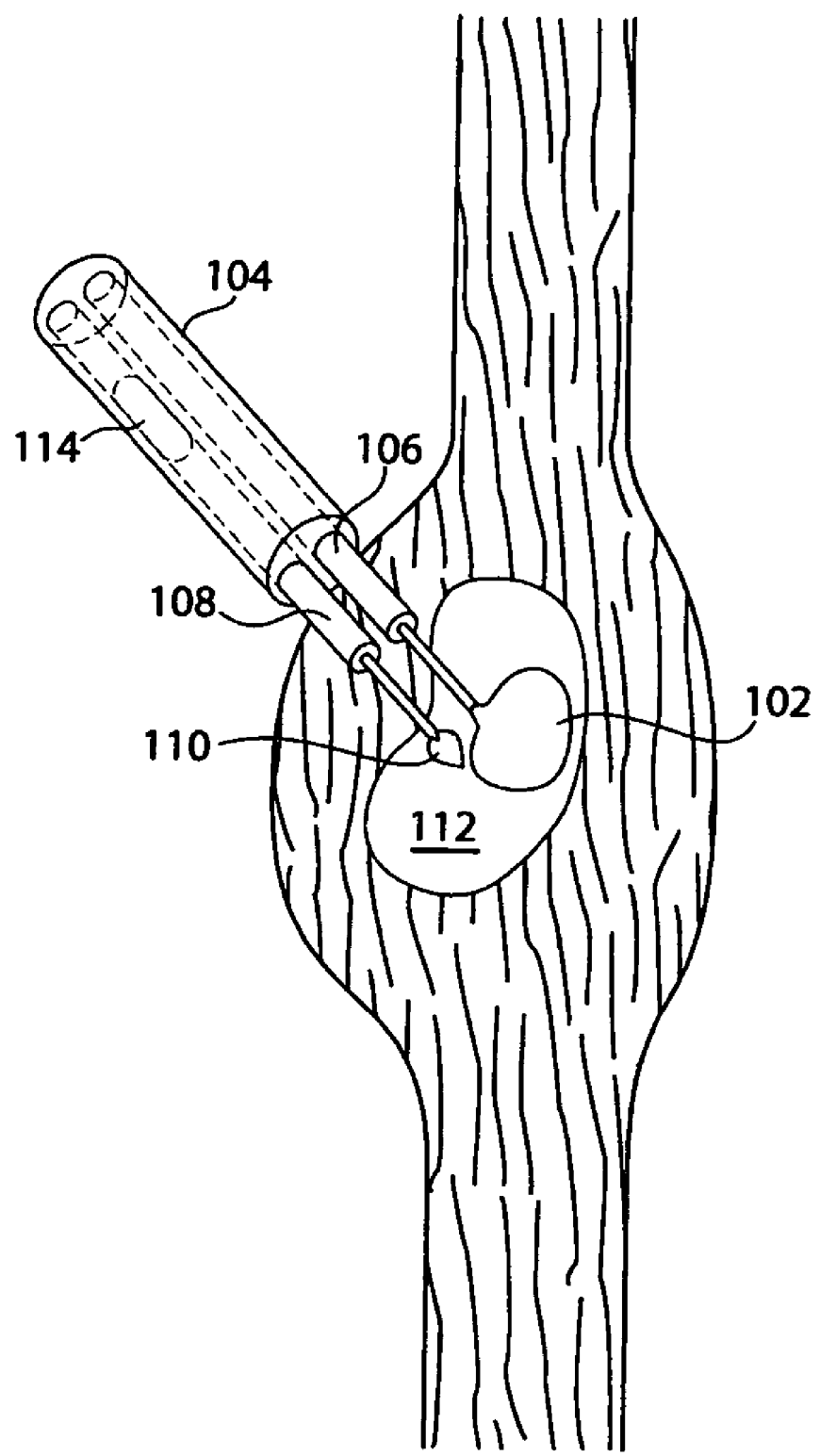
FIG. 18 represents a further arrangement for creating a pocket at a target site.

The formation of pockets in tissue are common, and can also be achieved in a further embodiment as represented in FIG. 18, through needle delivery of a balloon 102. In this embodiment a double lumen catheter 104 would be employed, one lumen 106 of which is fluidically connected to the balloon and the other lumen 108 connected to the exit port of the needle 110. Thus the balloon 102 can be inflated independently of the delivery of implant. A pocket 112 can thus be formed by introducing the needle/balloon 110 and 102 combination to a tissue site, inflating the balloon 102 to form a pocket 112, and then deflating the balloon 102 and filling the pocket 112 with a bolus of implant polymer 114.

Alternatively saline ejected through the first lumen 106 could precede the bolus 114 of polymer, and may be used to form the pocket 102 without the use of a balloon, but in this approach the saline must be removed before the implant is introduced into the site. Due to the high affinity of the polymer of the present invention to the uptake of water, the removal of saline is not as critical as for other implants. For example, for precipitating an implant there is normally an excess of carrier fluid present in the implant volume which must be absorbed by the body. This plus any residual saline in the pocket contributes to shrinking of the implant "effective volume" as the saline and carrier is absorbed by the body, which is typical in the prior art.

The foregoing description of a preferred embodiment of the invention has been presented for purposes of illustration and description. It is not intended to be exhaustive or to limit the invention to the precise forms disclosed. It is intended that the scope of the invention be defined by the following claims and their equivalents.

The invention claimed is:

1. A method of treating a sphincter in an esophagus of a patient to alleviate gastroesophageal reflux disease, said method comprising: providing a catheter and an injector coupled to said catheter, said catheter having a tissue piercing needle distal end; providing a liquid polymer which will polymerize in site at the site of injection to form a bulking implant, wherein the polymer comprises a polyisocyanate capped polyol; introducing said catheter into said esophagus of the patient; piercing an exterior surface of said sphincter of said esophagus of the patient with said tissue piercing needle distal end on said catheter; advancing said tissue piercing needle distal end a distance in an interior of said sphincter to a tissue site; and injecting a controlled volume of said liquid polymer into said tissue site to create a controlled volume of in-situ implant in said sphincter to bulk said sphincter; and thereby reducing at least one of the frequency and the quantity of sphincter reflux.

2. The method of claim 1, wherein said volume of liquid polymer is sufficient to create a bolus having a diameter in the range of about 1-10 mm in said esophageal sphincter.

3. The method of claim 2, wherein said bolus of polymer having a diameter of 1 to 10 mm is injected into an esophageal sphincter to reduce a duration of esophageal sphincter relaxation.

4. The method of claim 2, wherein said bolus of polymer is delivered to said sphincter to cause a reduction in the opening of said sphincter.

5. The method of claim 2, wherein said bolus of polymer is delivered to said sphincter to cause a tissue contraction around said implant.

6. The method of claim 1, wherein said volume of liquid polymer reduces at least one of: the frequency of sphincter relaxation; the frequency of reflux of stomach contents into an esophagus; the frequency of a symptom of reflux of stomach contents into an esophagus; and the incidence of a sequela of reflux of stomach contents into an esophagus.

7. The method of claim 1, wherein the polymer delivery device delivers said volume of polymer to a submucosa of said sphincter.

8. The method of claim 1, wherein said polymer implant comprises a biocompatible polymer which initiates a fibrotic response.

9. The method of claim 1, wherein said polymer implant further comprises free polyisocyanate.

10. The method of claim 1, wherein said catheter is directed to said sphincter transorally.

11. The method of treating a mammalian sphincter as recited in claim 1, wherein said catheter is directed to said sphincter transorally through an endoscope.

12. The method of claim 1, wherein said biocompatible polymer is polymerized in situ upon delivery of said polymer in said delivery device to said sphincter.

13. A method of treating a sphincter in an esophagus of a patient to alleviate gastroesophageal reflux disease, said method comprising: providing a catheter and an injector coupled to said catheter, said catheter having a tissue piercing needle distal end; providing a liquid polymer which will polymerize in site at the site of injection to form a bulking implant, wherein the polymer comprises a polyisocyanate capped polyol; introducing said catheter into said esophagus of the patient; piercing an exterior surface of said sphincter of said esophagus of the patient with said tissue piercing needle distal end on said catheter; advancing said tissue piercing needle distal end a distance in an interior of said sphincter to a tissue site; and injecting a controlled volume of said liquid polymer into said tissue site to create a controlled volume of in-situ implant in said sphincter to bulk said sphincter; and thereby reducing at least one of the frequency and the quantity of sphincter reflux; and wherein said polymer implant comprises a biocompatible polymer which polymerizes in situ by reaction with water, derive from one or both of water contained in the tissue of said sphincter, and aqueous solution mixed with the polymer at or near the time of administration of the polymer to the sphincter.

14. A method of treating a sphincter in an esophagus of a patient to alleviate gastroesophageal reflux disease, said method comprising: providing a catheter and an injector coupled to said catheter, said catheter having a tissue piercing needle distal end; providing a liquid polymer which will polymerize in site at the site of injection to form a bulking implant, wherein the polymer comprises a polyisocyanate capped polyol; introducing said catheter into said esophagus of the patient; piercing an exterior surface of said sphincter of said esophagus of the patient with said tissue piercing needle distal end on said catheter; advancing said tissue piercing needle distal end a distance in an interior of said sphincter to a tissue site; and injecting a controlled volume of said liquid polymer into said tissue site to create a controlled volume of in-situ implant in said sphincter to bulk said sphincter; and thereby reducing at least one of the frequency and the quantity of sphincter reflux; and wherein the polymer delivery device delivers said polymer to create a tightening of said sphincter without permanently damaging anatomical structures near said sphincter.

15. The method of claim 14, wherein said polymer delivery device delivers said polymer to an esophageal sphincter without permanently disrupting an aorta positioned near said esophageal sphincter.

16. The method of claim 14, wherein said polymer delivery device delivers said polymer to an esophageal sphincter without permanently damaging a vagus nerve positioned near said esophageal sphincter.

17. The method of claim 14, wherein said polymer delivery device delivers said polymer to an esophageal sphincter without permanently damaging an esophageal plexus of nerves and veins positioned near said esophageal sphincter.

18. The method of claim 14, wherein said polymer delivery device delivers said polymer to an esophageal sphincter while preserving a blood supply to said esophageal sphincter.

* * * * *